Figure 1:
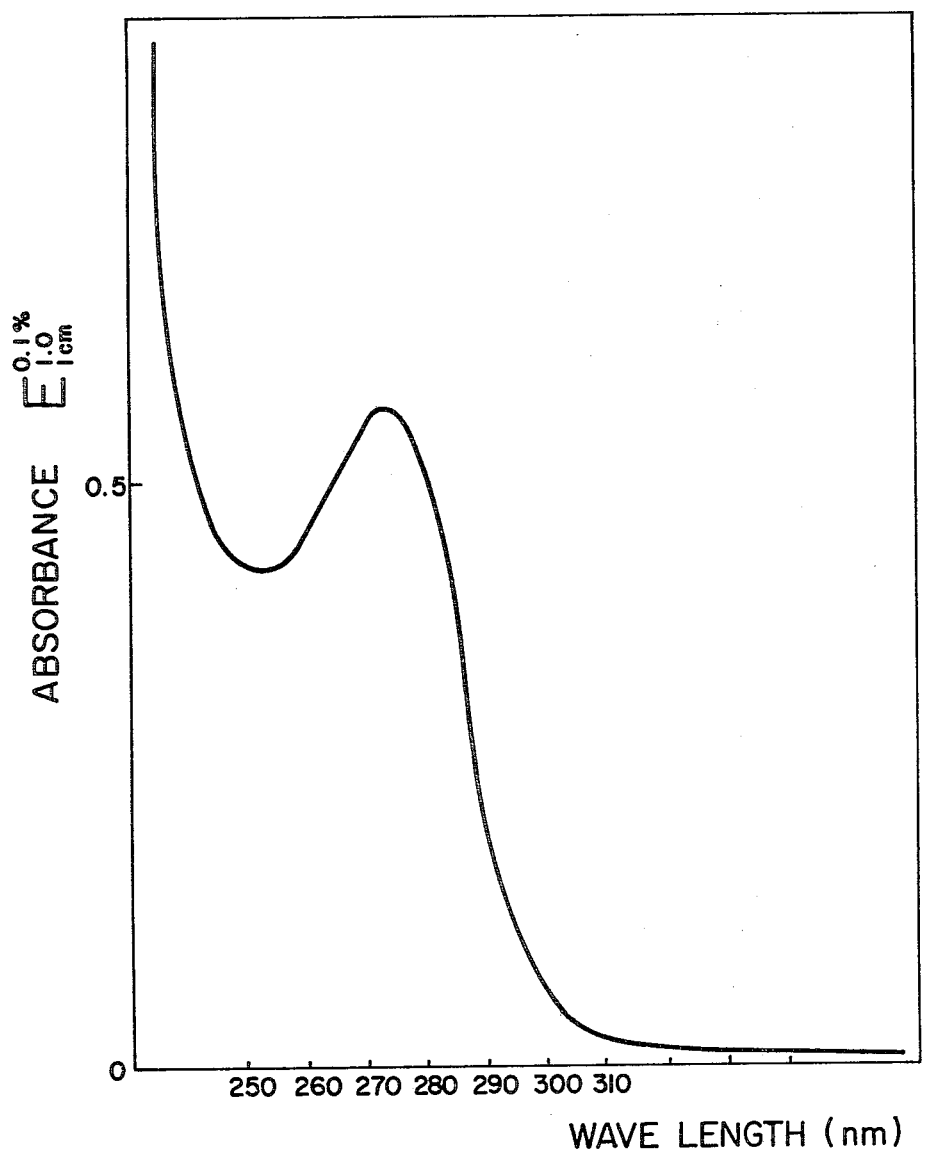

United States Patent [19]

Misato et al.

[11] 4,181,714

[45] Jan. 1, 1980

[54] ANTIBIOTICS BACILEUCINES A AND B AND PROCESS FOR PRODUCTION AND USE THEREOF

[75] Inventors: Tomomasa Misato, Tokyo; Keido Ko, Asaka; Yumiko Adachi, Kamifukuoka; Tadakazu Watanabe, Yokosuka, all of Japan

[73] Assignees: Kikagaku Kenkyusho, Wako; Ajinomoto, Kyobashi, both of Japan

[21] Appl. No.: 884,254

[22] Filed: Mar. 7, 1978

[30] Foreign Application Priority Data

Mar. 11, 1977 [JP] Japan .................................. 52-26771

[51] Int. Cl.$^2$ ............................................. A61K 35/00
[52] U.S. Cl. .................................. 424/117; 424/115; 435/68; 435/832
[58] Field of Search .............. 424/117, 115; 195/80 R

[56] References Cited

U.S. PATENT DOCUMENTS 4,031,206    7/1977    Celmer et al. ...................... 424/117

*Primary Examiner*—Jerome D. Goldberg
*Attorney, Agent, or Firm*—Bucknam and Archer

[57] ABSTRACT

The present invention refers to novel antibiotics, Bacileucines A and B and use thereof, which are effective as agricultural and horticultural fungicides. Bacileucines A and B are produced from the microorganism belonged to Genus Bacillus and are characterized by that they have no phytotoxicity of plant and no adverse effect on the human body, have an excellent control effect on diseases of plants such as rice plant, vegetables and green plants and cause no pollution on the environment.

16 Claims, 4 Drawing Figures

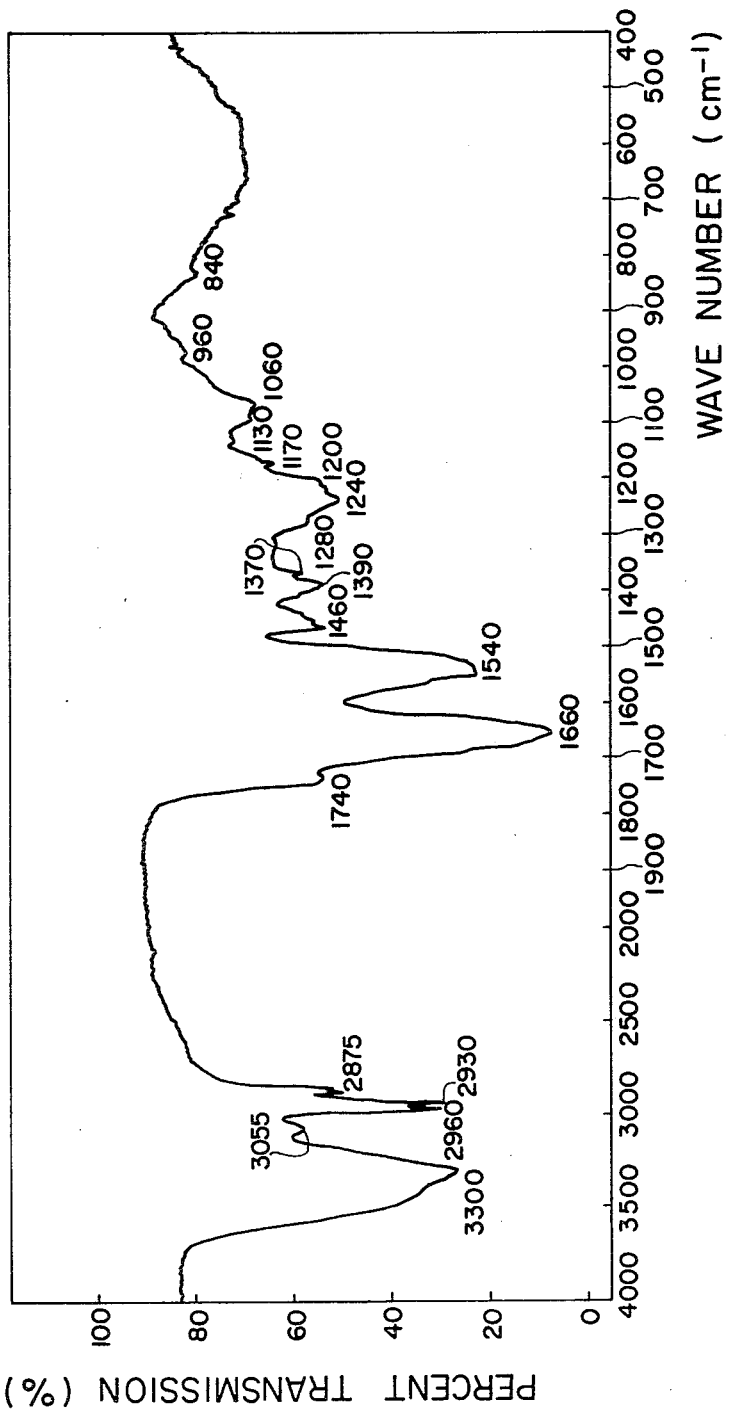

ANTIBIOTICS BACILEUCINES A AND B AND PROCESS FOR PRODUCTION AND USE THEREOF

The present invention relates to novel antibiotics Bacileucines A and B process for production thereof and agricultural and horticultural fungicidal use thereof.

Agricultural and horticultural fungicides containing a heavy metal compound, for example, copper preparations, mercury preparations and arsenic preparations, and organic chlorine chemicals and organic phosphate chemicals have heretofore been broadly used as agricultural and horticultural fungicides. However, each of these conventional agricultural and horticultural fungicides is toxic to animals and the human body. Further, they contaminate the soil and remain in the environment for a long time to exert a bad influence on animals and plants. Accordingly, environmental pollution with these chemicals is now a serious social problem and use of these chemicals is prohibited or restricted.

However, various diseases of plants, for example, diseases of rice, are becoming more prevalent with the reduction in the number of usable chemicals and therefore, development of a novel agricultural chemical having both a high controlling effect on plant diseases and high safety has been eagerly desired in the art. Therefore, we conducted research with a view to developing such an agricultural chemical. As a result, it was found that novel antibiotics discovered by us, Bacileucines A and B, have very excellent controlling effects on the main diseases of rice, namely blast and sheath blight, and the diseases of various other plants, such as gray mold and anthracnose of cucumber, black spot of pear and ripe rot of grape, these effects being confirmed in spraying tests. It was further found that the novel antibiotics discovered have no phytotoxicity to any kind of plant and have no adverse effect on the human body. Based on these findings, we have now completed the agricultural and horticultural fungicide of the present invention.

Bacileucines A and B, each of which is an effective ingredient of the present agricultural and horticultural fungicide, are novel antibiotics first developed by us. The preparation process and physicochemical properties of these novel antibiotics will now be described.

Figure 2:
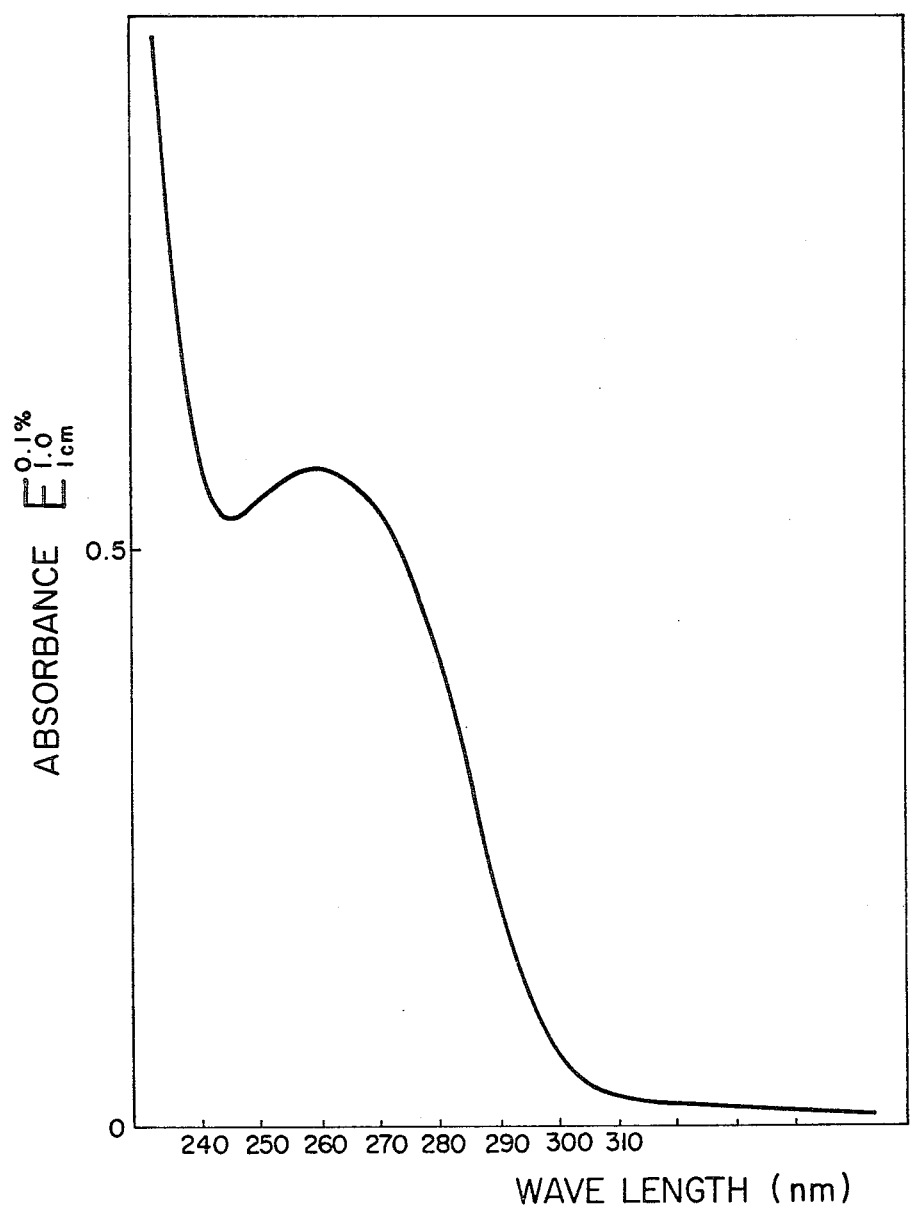
Figure 3:
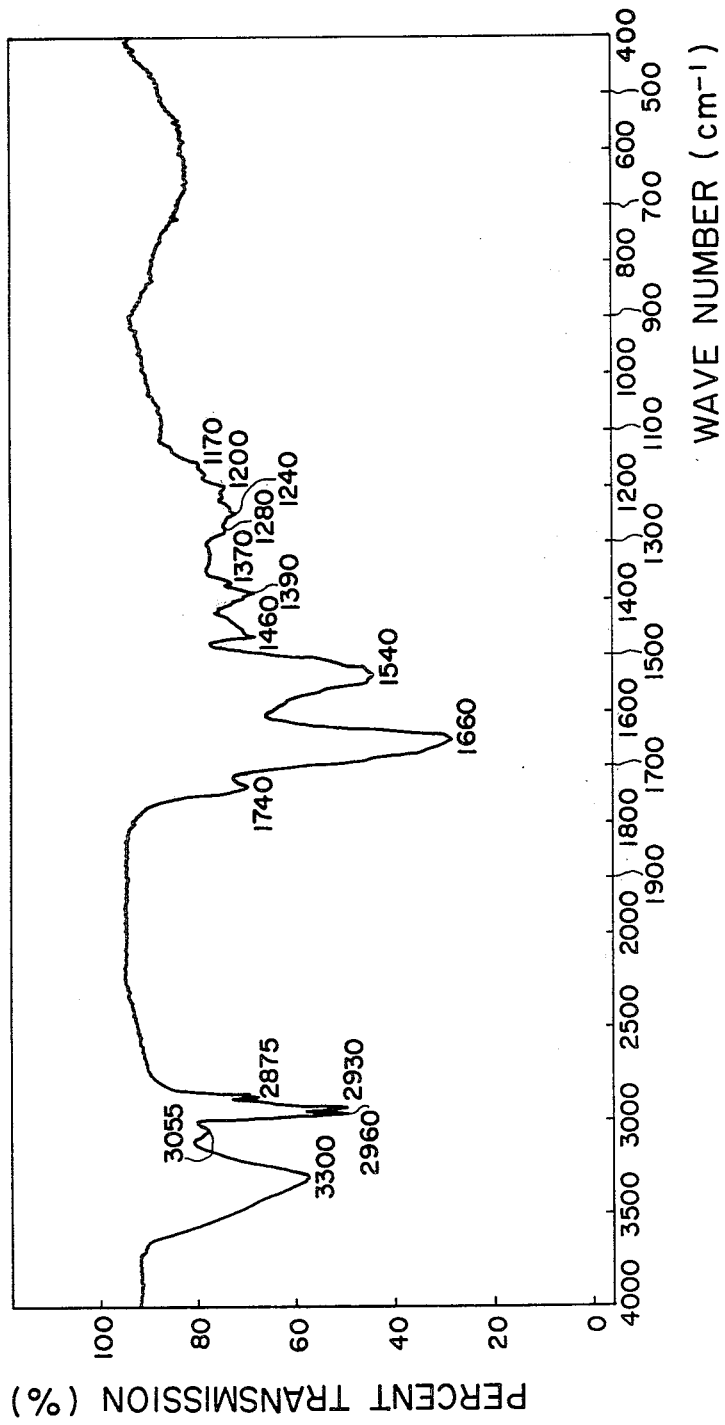

FIGS. 1 and 2 are graphs showing the ultraviolet absorption spectra of Bacileucines A and B of the present invention, respectively; and FIGS. 3 and 4 are graphs showing the infrared absorption spectra of Bacileucines A and B of the present invention, respectively.

The microorganism producing the antibiotics Bacileucines A and B used as the effective ingredient in the present invention is a Bacileucine A- and Bacileucine B-producing bacterium belonging to the genus Bacillus.

For example, there can be mentioned Bacillus sp. AW-3 having the above-mentioned property of producing Bacileucines A and B, by which Bacileucines A and B are advantageously produced. Accordingly, this strain can be effectively utilized for working the present invention.

The above-mentioned Bacillus sp. AW-3 (hereinafter referred to as "sp. AW-3") was found in the soil at Hirosawa, Wako-shi, Saitama-ken, Japan and it had been assigned the American Type Culture Collection (ATCC) (12301 Parklawn Drive Rockville, Md. 20852) as ATCC access number 31,268, and is on deposit with ATCC in an unrestricted deposit permitting the public full access to the culture. The species was released for distribution to the public on Feb. 8, 1977.

The sp. AW-3 has the following microbilogicical properties.

The microbiological properties described below were tested according to the methods described in M. J. Pelczar, "Manual of Microbiological Methods" (1975) and Ruth E. Gordon, "The Genus Bacillus" (1973), and the classification was conducted according to the methods described in Bergey's Manual of Determinative Bacteriology (8th edition) and the above-mentioned "The Genus Bacillus".

(A) MORPHOLOGY

The growth on a bouillon agar culture medium was observed.

(1) An aerobic bacillus having a size of $(0.6–0.7)\mu \times (1.8–5.0)\mu$.

(2) No pleomorphism of cells.

(3) Having motility and peritrichous flagella.

(4) Generating oval or columnar spores having a size of $(0.5–0.6)\mu \times (1.2–1.8)\mu$ and sporangia being not swollen, and the spores occurring in the middle or at the quasi-end of the sporangium.

(5) Gram positive.

(6) No acid fastness.

(B) GROWTH ON VARIOUS CULTURE MEDIA (1) Bouillon Agar Plate Culture: Rough, irregularly circular, semi-spherical or trapezoidal, entirely edged, homogeneous, brown, translucent or opaque, viscid.

(2) Bouillon Agar Slant Culture: Good, filiform or echinulate, membranous or raised, oleagenous, rough, viscid.

(3) Bouillon Liquid Culture: Good growth on the surface in a form of pellicle, not uniformly turbid.

(4) Bouillon Gelation Stab Culture: Strongly liquefying in a stratiform.

(5) Litmus Milk: Slightly reduced by litmus, completely liquefying, weakly alkaline (pH=8.0).

(6) B.C.P. Milk: Completely liquefying, weakly alkaline (pH=7.6).

(C) BIOCHEMICAL PROPERTIES (1) Nitrate Reduction: Strongly positive.

(2) Denitrification: Negative.

(3) MR Test: No change.

(4) VP Test: Positive at pH of 7.3 in 7 days.

(5) Formation of Indole: Negative.

(6) Formation of Hydrogen Sulfide: Positive (lead acetate agar medium (Difco medium)).

(7) Hydrolysis of Starch: Positive.

(8) Utilization of Citric Acid: Negative in Koser medium but strongly positive in Christensen medium.

(9) Utilization of Inorganic Nitrogen Sources: Nitrates and ammonium salts are utilized.

(10) Formation of Pigment or Dye: None.

(11) Urease: Quasi-positive.

(12) Oxidize: Positive.

(13) Catalase: Positive

(14) Growth Conditions: pH of 5.0 to 10.0, optimum pH being 7.2 to 7.5, temperature of 14.2° to 49.6° C. (no growth at 53° C.), optimum temperature being 20° to 25° C.

(15) Relation to Oxygen: Aerobic (facultative).

(16) O.F. Test: Growth is observed under either aerobic or anaerobic conditions (according to the method of Hugh Leifsen).

(17) Formation of Acid or Gas from Saccharides:

|  | Formation of Acid | Formation of Gas |
|---|---|---|
| L-Arabinose | ++ | − |
| D-Xyrose | ++ | − |
| D-Glucose | +++ | − |
| D-Mannose | + | − |
| D-Fructose | +++ | − |
| D-Galactose | − | − |
| Maltose | + | − |
| Sucrose | +++ | − |
| Lactose | + | − |
| Trehalose | + | − |
| D-Sorbitol | + | − |
| D-Mannitol | + | − |
| Inositol | ++ | − |
| Glycerin | + | − |
| Starch | ++ | − |
| Raffinose | + | − |
| Salicin | ++ | − |

+++ : highly utilized
++ : relatively highly utilized
+ : utilized
− : not utilized

(18) Formation of Acid on Ayers, Rupp & Johnson Medium:

| D-Glucose: | ++ |
|---|---|
| Trehalose: | ++ |
| L-Arabinose: | ++ |
| D-Mannitol: | ++ |
| D-Xyrose: | +++ |

+++ : highly utilized
++ : relatively highly utilized

(19) Salt Resistance (growth on glucose bouillon medium containing NaCl):

| NaCl (W/V, g/dl) | Growth |
|---|---|
| 0 | ++ |
| 3 | +++ |
| 5 | +++ |
| 7 | ++ |
| 10 | ++ |
| 15 | − |

+++ : very good growth
++ : good growth
− : no growth

(20) Deamination of Phenylalanine: None.
(21) Utilization of Propionic Acid: None.
(22) Growth on Sabouraud Dextrose Medium: Good.
(23) Formation of Water-Soluble Black Pigment: None on either glucose medium or tyrosine medium.
(24) Decomposition of Tyrosine: Negative.
(25) Decomposition of Casein: Positive.
(26) Growth on Anaerobic Agar (BBL) Medium: Not growth.

When the foregoing mycological properties of sp. AW-3 are examined according to the classification methods described in the above-mentioned references, it is seen that the strain is an aerobic bacillus, and from the fact that spores are formed, it is apparent that the strain belongs to the genus Bacillus. Further, as regards the species, sp. AW-3 is identified as a microorganism belonging to *Bacillus substilitis* (Ehrenberg), Cohn 1872 from the following properties: (1) the size of nutritive cells is $(0.6-0.7)\mu \times (1.8-5.0)\mu$, (2) sporangia are not swollen and spores occur in the central or subcentral portions of sporangia, (3) it grows well on a medium containing 7% of sodium chloride, (4) it grows well on Sabouraud dextrose medium, (5) it produces acetyl methylcarbinol, (6) it reduces nitrates, (7) it does not utilize propionic acid, (8) it does not decompose tyrosine and (9) it does not grow on an anaerobic agar medium.

The strain sp. AW-3 is one example of microorganisms that can be used in the present invention. Not only natural and artificial mutants of sp. AW-3 but also all the species belonging to the genus Bacillus and having a capacity of producing Bacileucines A and B described below can be used in the present invention.

In working the process of the present invention, a Bacileucine-producing bacterium belonging to the genus Bacillus is cultured according to an ordinary method customarily adopted in manufacture of antibiotics. The culturing mode is not particularly critical, but either liquid culturing or solid culturing can be adopted. In order to perform culturing industrially advantageously, it is recommended to adopt a method in which a culture medium is inoculated with a spore suspension or culture medium of a Bacileucine-producing bacterium and the culturing is carried out under aeration and agitation.

The nutritive source that is used in the present invention is not particularly critical, but any of nutritive sources customarily used for culturing microorganisms may be used. For example, as the carbon source there can be used carbon compounds that can be assimilated, such as glucose, sucrose, lactose, maltose, starch, dextrin, molasses, glycerin and cellulose, and as the nitrogen source, there can be used nitrogen-containing substances such as corn steep liquor, soybean powder, cotton seed powder, wheat gluten, peptone, meat extract, yeast extract, yeast, soybean protein hydrolyzate, casein hydrolyzate, ammonium salts and nitrates.

The culturing temperature may be appropriately changed within the Bacileucine-producing range of about 15° to 35° C., but preferred culturing temperatures are about 20° to about 30° C. The culturing time is changed depending on culturing conditions and the culturing is ordinarily carried out for about 24 to about 168 hours, preferably about 48 to 168 hours. The pH range is about 6.2 to 8.2, preferably about 7.1 to 7.3. In short, the culturing is completed while the potency of the Bacileucines is at a highest level.

The Bacileucines are accumulated in the medium where the Bacileucine-producing species has been thus cultured. Accordingly, cells are removed from the culture medium and the Bacileucines are separated and collected.

An example of the method for separating and purifying the Bacileucines will now be described.

The strain sp. AW-3 is cultured at 20° C. for 48 hours according to the shaking culture method, and the pH of the culture medium is adjusted to 7.1 to 7.3 and cells are removed. The pH of the resulting supernatant is adjusted to 4.0±0.1 and centrifugal separation is carried out under cooling. The precipitate is dissolved in a phosphoric acid buffer solution and the pH is adjusted to 7.1 to 7.3. The solution is subjected to centrifugal separation to remove the residue. The resulting supernatant is further subjected to the above treatment 3 times repeatedly.

The recovered supernatant is dissolved in a phosphoric acid buffer solution having a pH of 7.2±0.1 and the solution is subjected to gel filtration. Among ultraviolet absorption fractions, a preceding fraction of 273 nm is collected, and the pH is adjusted to 5.0±0.1 and centrifugal separation is carried out to collect Bacileucine A as the precipitate. The remaining supernatant is further subjected to centrifugal separation after adjustment of the pH to 4.0±0.1, and Bacileucine B is collected as the precipitate.

The flow sheet of the above steps is as shown below.

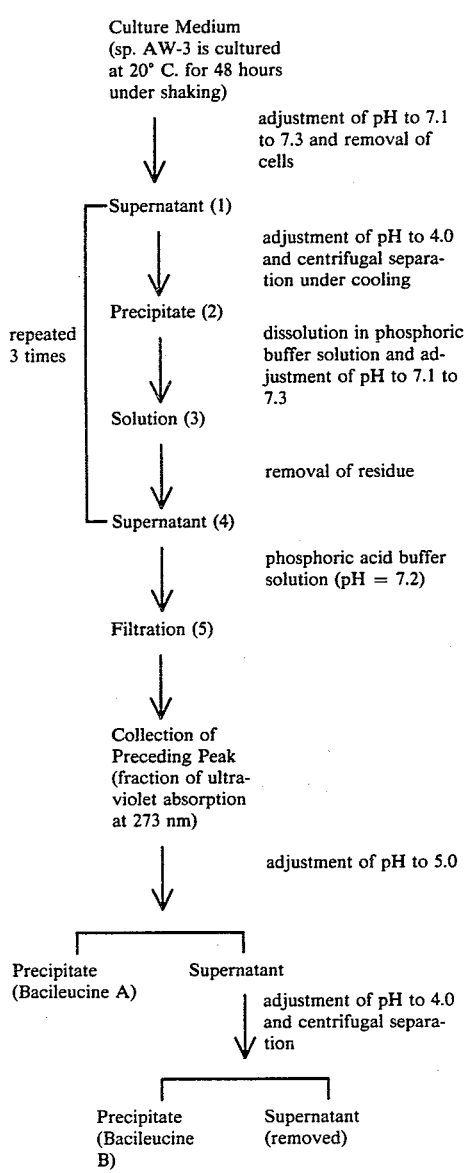

Each of so obtained Bacileucines A and B is light-yellow, amorphous powder and is a novel antibiotic having the following physicochemical properties.

(Physicochemical Properties of Bacileucines)

(1) Elementary Analysis Values:
Bacileucine A: C=56.28%, H=8.10%, N=9.20%, S=0.25%, O=26.22%

Bacileucine B: C=54.59%, H=7.79%, N=9.65%, S=0.24%, O=27.73%

(2) Molecular Weight: Each of Bacileucines A and B has the following molecular weight.
Measured: 13,000 (measured by chromatics)
Calculated: 13,000 (calculated from the sedimentation constant)

(3) Melting Point: Because each of Bacileucines A and B is a high-molecular-weight peptide, the melting point cannot be determined.

(4) Specific Rotatory Power: Any of Bacileucines A and B has no optical rotary power.

(5) Ultraviolet Absorption Spectrum: The ultraviolet absorption spectrum of Bacileucine A determined in 1/15 M phosphoric acid buffer solution (pH=7.17) is shown in FIG. 1 and the ultraviolet absorption spectrum of Bacileucine B determined in 1/15 M phosphoric acid buffer solution is shown in FIG. 2. The maximum absorption is observed at 273 nm ($E_1^{0.1\%}{}_{cm}$:1.0) in case of Bacileucine A and the maximum absorption is observed at 260 nm ($E_1^{0.1\%}{}_{cm}$:1.0) in case of Bacileucine B.

(6) Infrared Absorption Spectrum: The infrared absorption spectra of Bacileucines A and B determined according to the KBr method are shown in FIGS. 3 and 4. Bacileucine A has absorption bands at wave numbers of 3300, 3055, 2960, 2930, 2875, 1740, 1660, 1540, 1460, 1390, 1370, 1280, 1240, 1200 and 1170 cm$^{-1}$, and Bacileucine B has absorption bands at wave numbers of 3300, 3055, 2960, 2930, 2875, 1740, 1660, 1540, 1460, 1390, 1370, 1280, 1240, 1200, 1170, 1130, 1060, 960 and 840 cm$^{-1}$.

(7) Solvent Solubility: Each of Bacileucines A and B is soluble in water but insoluble in organic solvents such as methanol, ethanol, acetone, ethyl acetate, methyl acetate, pyridine, chloroform, benzene and n-hexane.

(8) Coloring Reaction: Each of Bacileucines A and B is positive to Folin's reagent and biuret reaction but negative to Molisch reaction and ninhydrin reaction.

(9) Basicity, Acidity or Neutrality: From the isoelectric point (PI), each of Bacileucines A and B is determined as an acidic substance.

(10) Color: Each of Bacileucines A and B is light-yellow, amorphous powder.

(11) Thermostability: In each of Bacileucines A and B, the antibiotic activity is reduced by 50% by the treatment at 60° C. and pH of 7.2 for more than 10 minutes.

(12) Isoelectric Point: The isoelectric point as determined by an electro-focussing protein-separating apparatus is as shown below:
Bacileucine A: pH of 5.2±0.2
Bacileucine B: pH of 4.3±0.2

(13) Rf Value: Because each of Bacileucines A and B is a high-molecular-weight peptide, the Rf value cannot be determined.

(14) Amino Acid Composition: Each of the amino acid compositions of Bacileucines A and B as determined by an automatic amino acid analyzer (Model Hitach KLA-3B) is as shown below.

| Amino Acid | Molecule Number |
|---|---|
| Leucine | 60 |
| Glutamic acid | 26 |
| Aspartic acid | 21 |
| Valine | 14 |
| Lysine | 10 |
| Tyrosine | 9 |
| Proline | 7 |

-continued

| Amino Acid | Molecule Number |
|---|---|
| Isoleucine | 4 |
| Alanine | 4 |
| Threonine | 3 |
| Serine | 2 |
| Glycine | 1 |
| Methionine | 1 |

(Biological Properties of Bacileucines)

(1) Antimicrobial Spectrum: The antimicrobial spectra of Bacileucines A and B to pathogenic bacteria as determined according to the paper disk method (Bacileucine concentration = 10 ppm) are as shown below.

| | Size (mm) of Growth-Inhibiting Circle | |
|---|---|---|
| | Bacileucine A | Bacileucine B |
| *Botrytis cinerea* causing gray mold in cucumber | 27 | 29 |
| *Colletotrichum lagenarium* causing anthracnose in cucumber | 26 | 28 |
| *Alternaria kikuchiana* causing black spot in pear | 23 | 25 |
| *Glomerella cingulata* causing ripe rot in grape | 20 | 22 |
| *Rhizoctonia solani* causing sheath blight in rice | 21 | 23 |
| *Pyricularia oryzae* causing blast in rice | 22 | 24 |
| *Escherichia coli* | 0 | 0 |

Bacileucines A and B are characterized in that they show specific activities to various pathogenic fungi on plants at in vitro tests. Further, Bacileucines A and B have prominent controlling effects to diseases caused by the above-mentioned pathogenic fungi of plants at spraying tests conducted in green houses, and it has been confirmed that each of Bacileucines A and B is practically valuable as an agricultural and horticultural fungicide.

(2) Toxicity: The acute toxicity of each of Bacileucines A and B to mice is such that mice are not killed by abdominal or oral administration of 1,000 mg/Kg, and it has been confirmed that both the Bacileucines A and B are very lowly toxic.

Since each of Bacileucines A and B is a high-molecular-weight peptide, they are compared with enzymes. Although a substance included in the enzyme has an enzymatic activity, each of Bacileucines A and B has no enzymatic activity. Further, a substance included in an antibiotic is a metabolic product of a microorganism and has the activity of inhibiting the growth of other microorganisms, and its molecular weight or degree of the activity is not limited. Accordingly, in view of the physicochemical and biological properties of Bacileucines A and B, it is judged that it is reasonable to classify each of Bacileucines A and B as an antibiotic.

When the above-mentioned physicochemical and biological properties of Bacileucines A and B are compared with those of known antibiotics disclosed in literature references, especially antibiotics produced by microorganisms belonging to the genus Bacillus, it is seen that they are different from Bacillomycin with respect to the molecular weight, and they are different from Mycobacillin because Mycobacillin is a circular polypeptide having a molecular weight of 1800 and is soluble in an alcohol. Further, Bacileucines A and B are distinguishable over Fraction A (Mira Sen & P. Nandi, "Isolation of the Active Principles from a Strain of *Bacillus subtilis*", Indian J. Chem., vol. 1, pages 135-136) with respect to the ultraviolet absorption pattern and maximum absorption band (226 nm) and in the point that Fraction A is soluble in various solvents.

Furthermore, Bacileucines A and B are distinguishable over known antibiotics in the point that they have a prominent specific antimicrobial activity to pathogenic bacteria of plants.

Thus, it is impossible to find out any known substance that can be regarded as being identical with Bacileucine A or B.

For the reasons set forth above, it was concluded that each of Bacileucines A and B is apparently a novel antibiotic, and they were named "Bacileucine A" and "Bacileucine B", respectively.

One embodiment of the process for purification of Bacileucines A and B will now be described by reference to the following Example.

EXAMPLE 1

In Erlenmeyer flasks having a capacity of 300 ml, 1 liter of a dry bouillon medium (the pH being adjusted to 7.0) containing 5 g of meat extract, 15 g of peptone, 5 g of sodium chloride and 5 g of $K_2HPO_4$ and 1 liter of a potato glucose culture medium (the ph being not adjusted) were charged. The mixed culture medium was sterilized at 120° C. for 15 minutes and inoculated with sp. AW-3. The culturing was carried out under shaking at a rotation rate of 115 rpm at 20° C. for 48 hours to obtain a culture medium containing Bacileucines.

The pH of the culture medium was adjusted to 7.1 to 7.3 and centrifugal separation is carried out at a rotation rate of 10000 rpm for 30 minutes to remove cells.

It was found that Bacileucines were present in the resulting supernatant in an amount of 100 to 500 γ/ml.

The pH of the supernatant obtained above was adjusted to 4.0 by 1 N NaCl and centrifugal separation was carried out under cooling at a rotation rate of 5000 rpm. The precipitate was dissolved in a 1/15 M phosphate buffer solution and the pH was adjusted to 7.1 to 7.3. The resulting solution was subjected to centrifugal separation at a rotation rate of 10000 rpm to remove the residue and recover the supernatant. The foregoing treatment was repeated 3 times on the supernatant. The recovered solution was dissolved in a 1/15 M phosphoric acid buffer solution (having a pH of 7.2) and filtered with Sephadex G-50 (trademark).

Among ultraviolet absorption fractions, a preceding fraction at 273 nm was collected and the pH was adjusted to 5.0 by 1 N HCl, and centrifugal separation was carried out at a rotation rate of 5000 rpm to obtain a precipitate and a supernatant. The precipitate was recovered and dried to obtain light-yellow amorphous powder of Bacileucine A in an amount of 200 mg/liter.

Separately, the pH of the supernatant was adjusted to 4.0 and centrifugal separation was carried out at a rotation rate of 5000 rpm to obtain a precipitate and a supernatant. The supernatant was removed, and the precipitate was recovered and dried to obtain a light-yellow amorphous powder of Bacileucine B in an amount of 100 mg/liter.

The so obtained antibiotic Bacileucine A or B or a complex thereof is formed into an agricultural and horticultural fungicide comprising this antibiotic as an effective ingredient.

By the term "Bacileucine complex" used herein is meant a filtration-refined product containing at least Bacileucines A and B as ingredients having the same activity, which is separated and collected from the above-mentioned culture medium, namely the refined product obtained at the filtration step (5) in the above-mentioned refining process flow sheet. Both the Bacileucines A and B are prepared from one and the same culture medium, and complex thereof can be used as an effective ingredient as it is. Accordingly, the use of this complex is very advantageous from the economical viewpoint.

When the effective ingredient of the present invention is used as an agricultural and horticultural fungicide, according to known techniques customarily adopted for manufacture of ordinary agricultural chemicals, it is formed into an optical preparation, for example, granule, dust, emulsifiable liquid, wettable powder, tablet, oil, spray or fumigant by using an appropriate solid carrier, liquid carrier or emulsifying dispersant customarily used in the art. As the carrier, there can be mentioned, for example, clay, kaolin, bentonite, acid clay, diatomaceous earth and calcium carbonate. As the solid carrier, there can be mentioned, for example, nitrocellulose, starch and gum arabic, and as the liquid carrier, there can be mentioned, for example, water, methanol, ethanol, acetone, dimethylformamide and ethylene glycol. Further, adjuvants customarily used for manufacture of agricultural chemicals, such as sulfuric acid esters of higher alcohols, polyoxyethylene alkyl aryl ethers, alkyl aryl polyethylene glycol ethers, alkyl aryl sorbitan monolaurates, alkyl aryl sulfonates, alkyl sulfonic acid salts, alkyl aryl sulfonic acid salts, quaternary ammonium salts and polyalkyleneoxides, may be appropriately incorporated. An appropriate mixing ratio of the effective ingredient is about 10 to about 90% in case of an emulsifiable liquid or wettable powder and about 0.1 to about 10% in case of a dust or oil. Of course, the mixing ratio of the effective ingredient may be changed according to the intended object of application.

The fungicide of the present invention may further comprise other fungicides, herbicides, insecticides, fertilizers or soil modifiers according to need, and it can be used as a mixed agricultural chemical.

The agricultural and horticultural fungicide of the present invention will now be described by reference to the following Examples.

Formulation 1 (Wettable Power)

A mixture of 10 parts of Bacileucine A (or Bacileucine B or a complex thereof), 5 parts of sodium lauryl sulfate, 2 parts of sodium dinaphthylmethane-disulfonate-formalin condensate and 83 parts of clay was blended and pulverized to obtain 100 parts of a wettable powder.

Formulation 2 (Dust)

A mixture of 0.2 part of Bacileucine A (or Bacileucine B or Bacileucine complex), 0.5 part of calcium stearate, 50 parts of talc and 9.3 parts of clay was blended and pulverized to obtain 100 parts of a dust.

Formulation 3 (Emulsifiable Liquid)

A mixture of 8 parts of Bacileucine B (or Bacileucine A or Bacileucine complex), 10 parts of ethylene glycol, 20 parts of dimethylformamide, 10 parts of alkyldimethylbenzyl ammonium chloride and 52 parts of methanol was blended and dissolved to obtain 100 parts of an emulsifiable liquid.

Formulation 4 (Granule)

A mixture of 10 parts of Bacileucine B (or Bacileucine A or Bacileucine complex), 15 parts of starch, 72 parts of bentonite and 3 parts of sodium lauryl sulfate was blended and pulverized to obtain 100 parts of a granule.

Controlling effects of the agricultural and horticultural fungicide of the present invention on various plant diseases will now be described in detail by reference to the following tests.

EXAMPLE 2 (Test on Control Effect on Blast of Rice)

In each of a number of synthetic resin pots having a diameter of 6 cm, 10 stalks of rice (Jukkoku variety) were cultivated in a green house, and in the four-leaved stage, a wettable powder prepared according to the method described in Example 1 was diluted with water and the dilution was sprayed on the plants by a spray gun in an amount of 50 ml per pot. After the sprayed chemical was dried, a suspension formed by suspending in water spores of a pathogenic bacterium causing blast on rice (*Pyricularia oryzae*) cultured in a rice hull culture medium (containing a yeast extracts, a meat extract, soluble starch, sucrose and rice hulls) was uniformly sprayed and inoculated on the rice plants. Then, the pots were kept in a thermostat box maintained at a temperature of 27° C. and at a relative humidity higher than 95% to cause the disease in the rice plant. When two days had passed from appearance of disease spots, the number of disease spots per leaf was counted and the control value was calculated according to the following formula:

$$\text{Control value (\%)} = \frac{\text{(disease spot number in non-treated area} - \text{disease spot number in treated area)}}{\text{disease spot number in non-treated area}} \times 100$$

Obtained results are shown in Table 1.

Table 1

| Chemical Tested | Concentration (ppm) in Sprayed Dilution | Control Value (%) | Phytotoxicity |
|---|---|---|---|
| Bacileucine A | 250 | 87 | not observed |
| Bacileucine A | 500 | 96 | not observed |
| Bacileucine A | 1000 | 99 | not observed |
| Bacileucine B | 250 | 93 | not observed |
| Bacileucine B | 500 | 95 | not observed |
| Bacileucine B | 1000 | 98 | not observed |
| Bacileucine Complex[a] | 1000 | 99 | not observed |
| Blasticidin S[1] | 20 | 95 | not observed |
| Kitazin-P[2] | 500 | 80 | not ob- |

Table 1-continued

| Chemical Tested | Concentration (ppm) in Sprayed Dilution | Control Value (%) | Phytotoxicity |
|---|---|---|---|
| | | | served |

Notes
(a)refined product obtained at filtration step (5) in the above-mentioned flow sheet of the refining process
(1)blasticidin-S-benzylaminobenzene-sulfonate
(2)O,O-diisopropyl-S-benzylphosphorothiolate

EXAMPLE 3 (Test on Control Effect on Sheath Blight of Rice)

In each of a number of synthetic resin pots having a diameter of 6 cm, 10 stalks of rice (Jukkoku variety) cultivated in a green house, and an aqueous dilution of a wettable powder prepared according to the method described in Example 1 was sprayed on the rice plant in the four-leaved stage by s spray gun in an amount of 50 ml per pot. After the sprayed chemical was dried, agar-adhering mycelium pieces cut by a cork borer from a colony of a pathogenic bacterium causing sheath blight in rice (Rhizoctonia solani), which had been cultured in a potato agar culture medium, were attached to the stalks to inoculate the rice plants with the disease-causing bacterium. The inoculated rice plants were kept in a thermostat box maintained at a temperature of 27° C. and at a relative humidity higher than 95% to cause the disease in the rice plant. When two days had passed from inoculation, the degree of propagation of disease spots from the inoculation point was examined and compared with that in a non-treated area. The control value was calculated according to the following formula. The degree of propagation of the disease was evaluated based on the seven-staged scale (0 to 6).

$$\text{Control value (\%)} = \left(1 - \frac{\text{disease index in treated area}}{\text{disease index in non-treated area}}\right) \times 100$$

The disease index mentioned above is a value corresponding to the sum of $0a+1b+2c+3d+4e+5f+6g$, in which a, b, c, d, e, f and g are numbers of plants of the disease degrees of 0 to 6, respectively.

Obtained results are shown in Table 2.

Table 2

| Chemical Tested | Concentration (ppm) of Chemical in Sprayed Liquid | Control Value (%) | Phytotoxicity |
|---|---|---|---|
| Bacileucine A | 250 | 85 | not observed |
| Bacileucine A | 500 | 91 | " |
| Bacileucine A | 1000 | 95 | " |
| Bacileucine B | 250 | 92 | " |
| Bacileucine B | 500 | 94 | " |
| Bacileucine B | 1000 | 99 | " |
| Bacileucine Complex | 1000 | 99 | " |
| Polyoxin D(3) | 40 | 95 | " |

Notes
(3)Polyoxin D wettable powder

EXAMPLE 4 (Test on Control Effect on Gray Mold in Cucumber)

Seedlings of cucumber (Sagami Hanpaku variety) obtained 12 days after seedling were used for the test, and cultivation was carried out under controlled temperature and humidity conditions so that the maximum daytime temperature was 28° C., the minimum night temperature was 20° C. and the relative humidity was 60%.

A pathogenic fungus causing gray mold in cucumber (Botrytis cinerea) was cultured in a PDA plate culture medium for 3 days at 23° C. and the colony was cut off by a cork borer and transplanted to a PG liquid medium. Culturing was further conducted for 3 days under shaking. The resulting cells were pulverized by a homogenizer and diluted with distilled water so that the $OD_{610}$ value was 1.3 to 1.5.

A chemical composition having a predetermined active ingredient concentration (prepared according to the method described in Example 3) was sprayed on the cucumber plants, and after the applied chemical was dried, the cucumber plants were shifted into an inoculation box (maintained at 20° C.). The above dilution was inoculated in an amount of 10 cc per 10 seedling under a compressor guage pressure of 0.8 $Kg/cm^2$. After the inoculation, the relative humidity was maintained at 100%, and the inoculated cucumber was allowed to stand in this state for 3 days.

The control value was calculated according to the following formula. The degree of propagation of the disease was evaluated based on the seven-staged scale (0 to 6).

$$\text{Control value (\%)} = \left(1 - \frac{\text{disease index in treated area}}{\text{disease index in non-treated area}}\right) \times 100$$

The disease index mentioned above is a value corresponding to the sum of $0a+1b+2c+3d+4e+5f+6g$, in which a, b, c, d, e, f and g are numbers of plants of the disease degrees of 0 to 6, respectively.

Obtained results are shown in Table 3.

Table 3

| Chemical Tested | Concentration (ppm) of Chemical in Sprayed Liquid | Control Value (%) | Phytotoxicity |
|---|---|---|---|
| Bacileucine A | 250 | 87 | not observed |
| Bacileucine A | 500 | 92 | " |
| Bacileucine A | 1000 | 96 | " |
| Bacileucine B | 250 | 90 | " |
| Bacileucine B | 500 | 94 | " |
| Bacileucine B | 1000 | 100 | " |
| Bacileucine Complex | 1000 | 100 | " |
| Difolatan wettable (powder)(4) | 1000 | 90 | " |
| Difolatan wettable (powder)(4) | 2000 | 100 | observed |

Notes
(4)N-(1,1,2,2,-tetrachloroethylthio)-4-cyclohexene-1,2-dicarboxyimide

EXAMPLE 5 (Test on Control Effect on Anthracnose in Cucumber)

Cucumber seedlings (Sagami Hanpaku variety) planted one plant per pot were used for the test, and each test area included three pots. After seeding was carried out by using Kureha Soil, the pots were kept for 2 weeks in an air-conditioned green house (maximum daytime temperature=28° C., minimum night temperature=20° C., light illumination time=12 hours per day, light source=sunglow lamp) to grow the cucumber plants.

A chemical composition having a predetermined concentration, which was prepared according to the method described in Example 3 was sprayed on the plants by a spray gun and the plants were air-dried for 2 hours in a green house.

Spores of a pathogenic fungus causing anthracnose in cucumber (*Colletotrichum lagenarium*), which had been cultured for 10 days at 23° C. in an agar slant culture medium of sweet corn, were taken into sterilized water, and one drop of a spreader was added to 50 cc of the spore suspension. In an inoculation box, the spore suspension was sprayed on the plants in an amount of 50 cc per 50 seedling by a spray gun to effect inoculation.

After inoculation, water was sufficiently sprayed in the inoculation box and incubation was carried out in the dark at a temperature of 25° C. and a relative humidity of 80% or higher for 24 hours. Then, the test plants were shifted onto a water-filled open shelf and was kept at a relative humidity of 60% and a temperature of 25° C. for 72 hours to cause the disease.

The total number of disease spots on leaves of the plants of each area was counted and the control value was calculated according to the following formula:

$$\text{Control value (\%)} = \left(1 - \frac{\text{total number of disease spots in test area}}{\text{total number of disease spots in control area}}\right) \times 100$$

Obtained results are shown in Table 4.

Table 4

| Chemical Tested | Concentration (ppm) in Sprayed composition | Control Value (%) | Phytotoxicity |
|---|---|---|---|
| Bacileucine A | 250 | 95 | not observed |
| Bacileucine A | 500 | 97 | " |
| Bacileucine A | 1000 | 100 | " |
| Bacileucine B | 250 | 98 | " |
| Bacileucine B | 500 | 100 | " |
| Bacileucine B | 1000 | 100 | " |
| Bacileucine Complex | 1000 | 99 | " |
| Maneb-Dithane[5] | 1000 | 95 | " |

Notes
[5] manganous ethylene-1,2-bis-dithiocarbomate

Consideration

From the foregoing test results, it is apparent that the fungicide of the present invention has very high control values with respect to various diseases of plants and it has no phytotoxicity, and that it excels over commercially available chemicals.

For example, the application range of the fungicide of the present invention is very broad and it has a controlling effect on various diseases of plants, while Blasticidin S which is a commercially available antibiotic chemical has a specific effect on blast of rice alone and Polyoxin D has a specific effect on sheath blight of rice alone. Further, although commercially available synthetic chemicals such as Kitazin, Difolatan and Dithane exert controlling effects at high concentrations and Dithane causes phytotoxicity, the fungicide of the present invention exerts comparable or superior effects at relatively low concentrations and does not cause phytotoxicity even at high concentration. Accordingly, the fungicide of the present invention is valuable as a new type of antibiotic in agricultural and horticultural fungicide.

What we claim are:

1. An antibiotic, Bacileucine A, which has a specific antimicrobial spectrum to pathogenic bacteria of plants and is an acidic substance characterized by the following physicochemical properties: elementary analysis values of C=56.28%, H=8.10%, N=9.20%, S=0.25% and O=26.22%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200 and 1170 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH of 5.2 ($\pm$0.2).

2. An antibiotic, Bacileucine B, which has a specific antimicrobial spectrum to pathogenic bacteria of plants and is an acidic substance characterized by the following physicochemical properties: elementary analysis values of C=54.59%, H=7.79%, N=9.65%, S=0.24% and O=27.73%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200, 1170, 1130, 1060, 960 and 840 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH 4.3 ($\pm$0.2).

3. An antibiotic complex of Bacileucine A, which has a specific antimicrobial spectrum to pathogenic bacteria of plants and is an acidic substance characterized by the following physicochemical properties: elementary analysis values of C=56.28%, H=8.10%, N=9.20%, S=0.25% and O=26.22%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200 and 1170 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH of 5.2 ($\pm$0.2) and Bacileucine B, which has a specific antimicrobial spectrum to pathogenic bacteria of plants and is an acidic substance characterized by the following physicochemical properties: elementary analysis values of C=54.59%, H=7.79%, N=9.65%, S=0.24% and O=27.73%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200, 1170, 1130, 1060, 960 and 840 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH 4.3 ($\pm$0.2), produced by cultivating Bacillus sp. AW-3 (ATCC 31,268) under aeration and agitation in a culture medium at a pH of 6.2 to 8.2 until substantial antibiotic activity is obtained in the culture medium and separating said antibiotic complex therefrom.

4. A process for the preparation of antibiotic complex of Bacileucines A and B which comprises the following steps: (a) culturing Bacillus sp. AW-3 (ATCC 31,268) in a culture medium at a pH of about 6.2 to 8.2, at a temperature of about 15° to 35° C. and for a time sufficient to obtain substantial antibiotic activity in the culture medium; (b) maintaining the pH of the culture medium in the neighbourhood of 7 and filtering out the cells; (c) bringing the pH of the filtrate to about 4.0, and centrifuging to obtain a residue; (d) dissolving the residue in a buffer solution having a pH of about 7 and filtering out impurities; (e) repeating the steps (c) and (d) several times to obtain a complex of Bacileucines A and B as a residue in pure state; (f) separating a pure complex of Bacileucines A and B.

5. A process for the preparation of antibiotic complex according to claim 4 wherein Bacillus sp. AW-3 is cultured for about 24 to 168 hrs.

6. A process for the preparation of the antibiotic complex according to claim 5 wherein Bacillus sp. AW-3 is cultured for about 48 to 168 hrs.

7. A process for the preparation of the antibiotic complex according to claim 4 wherein Bacillus sp. AW-3 is cultured at a pH of about 7.1 to 7.3.

8. A process for the preparation of the antibiotic complex according to claim 4 wherein Bacillus sp. AW-3 is cultured at a temperature of about 20° to 30° C.

9. A process for the preparation of the antibiotics Bacileucines A and B which comprises the following steps: (a) culturing Bacillus sp. AW-3 (ATCC 31,268) in a culture medium at a pH of about 6.2 to 8.2, at a temperature of about 15° to 35° C. and for a time sufficient to obtain substantial antibiotic activity in the culture medium; (b) maintaining the pH of the culture medium in the neighbourhood of 7 and filtering out the cells; (c) bringing the pH of the filtrate to about 4.0, and centrifuging to obtain a residue; (d) dissolving the residue in a buffer solution having a pH of about 7 and filtering out impurities; (e) repeating the steps (c) and (d) several times; (f) lowering the pH of the obtained pure filtrate to about 5.0 to precipitate and filter out Bacileucine A to obtain Bacileucine A, and a filtrate; and (g) lowering the pH of the filtrate to about 4.0 to precipitate and filter out Bacileucine B.

10. A process for the preparation of the antibiotics according to claim 9 wherein Bacillus sp. AW-3 is cultured for about 24 to 168 hrs.

11. A process for the preparation the antibiotics according to claim 10 wherein Bacillus sp. AW-3 is cultured for about 48 to 168 hrs.

12. A process for the preparation of the antibiotics according to claim 9 wherein Bacillus sp. AW-3 is cultured at a pH of about 7.1 to 7.3.

13. A process for the preparation of the antibiotics according to claim 9 wherein Bacillus sp. AW-3 is cultured at a temperature of about 20° to 30° C.

14. An agricultural and horticultural fungicidal composition comprising at least one antibiotic selected from the group consisting of Bacileucine A, which has a specific antimicrobial spectrum to pathogenic bacteria of plants and is an acidic substance characterized by the following physiochemical properties: elementary analysis values of C=56.28%, H=8.10%, N=9.20%, S=0.25% and O=26.22%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200 and 1170 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH of 5.2 ($\pm$0.2), Bacileucine B, which has s specific antimicrobial spectrum to pathogenic bacteria of plants and is an acidic substance characterized by the following physicochemical properties: elementary analysis values of C=54.59%, H=7.79%, N=9.65%, S=0.24% and O=27.73%, a molecular weight of 13,000, an infrared absorption spectrum having absorption bands at wave numbers of 3300, 3055, 2960, 2930, 2875, 1740, 1660, 1540, 1460, 1390, 1370, 1280, 1240, 1200, 1170, 1130, 1060, 960 and 840 cm$^{-1}$, such a solvent solubility that the antibiotic is soluble in water but insoluble in organic solvents, such coloring reaction characteristics that the antibiotic is positive to Folin's reagent and biuret reaction and negative to Molisch reaction and ninhydrin reaction, and an isoelectric point at a pH 4.3 ($\pm$0.2) and a complex as defined in claim 12 thereof as an effective ingredient in an amount of 0.1 to 90 percent by weight and an inert carrier.

15. An agricultural and horticultural fungicidal composition according to claim 14 wherein the composition is in the form of an emulsion or wettable powder containing said effective ingredient in an amount of 10 to 90 percent by weight.

16. An agricultural and horticultural fungicidal composition according to claim 14 wherein the composition is in the form of dust or oil containing said effective ingredient in an amount of 0.1 to 10 percent by weight.

* * * * *